United States Patent
De Keyzer

(10) Patent No.: US 7,651,765 B2
(45) Date of Patent: Jan. 26, 2010

(54) ADHESIVE COMPOSITION AND TAPES AND LABELS DERIVED THEREFROM

(75) Inventor: Noël R. M. De Keyzer, Ottignies Louvain-la-Neuve (BE)

(73) Assignee: Kraton Polymers U.S. LLC, Houston, TX (US)

( * ) Notice: Subject to any disclaimer, the term of this patent is extended or adjusted under 35 U.S.C. 154(b) by 905 days.

(21) Appl. No.: 10/546,022

(22) PCT Filed: Feb. 19, 2004

(86) PCT No.: PCT/EP2004/050168

§ 371 (c)(1),
(2), (4) Date: Aug. 18, 2005

(87) PCT Pub. No.: WO2004/074394

PCT Pub. Date: Sep. 2, 2004

(65) Prior Publication Data

US 2006/0155062 A1     Jul. 13, 2006

(30) Foreign Application Priority Data

Feb. 21, 2003   (EP)   ................................. 03100428
Jun. 12, 2003   (EP)   ................................. 03101715

(51) Int. Cl.
B32B 7/12   (2006.01)
(52) U.S. Cl. ............... 428/355 BL; 428/355 R
(58) Field of Classification Search ............. 428/355 R, 428/355 BL
See application file for complete search history.

(56) References Cited

U.S. PATENT DOCUMENTS

| | | | |
|---|---|---|---|
| 5,389,438 A | 2/1995 | Miller et al. | |
| 5,583,182 A | 12/1996 | Asahara et al. | |
| 5,589,542 A | 12/1996 | Himes | |
| 5,663,228 A | 9/1997 | Sasaki et al. | |
| 6,384,138 B1 | 5/2002 | Jacob et al. | |
| 6,833,411 B2 | 12/2004 | Fujiwara et al. | |
| 2003/0232928 A1 | 12/2003 | Atwood et al. | |
| 2004/0116582 A1 | 6/2004 | De Keyzer et al. | |

FOREIGN PATENT DOCUMENTS

| EP | 0 027 606 A1 | 4/1981 |
|---|---|---|
| EP | 0 306 232 A2 | 3/1989 |
| EP | 0 368 141 A2 | 5/1990 |
| EP | 0 443 263 A2 | 8/1991 |
| EP | 0 711 795 A1 | 5/1996 |
| GB | 1193628 | 6/1970 |
| JP | 2102212 A | 4/1990 |
| JP | 2135256 A | 5/1990 |
| JP | 5345885 A | 12/1993 |
| JP | 7238129 A | 9/1995 |
| JP | 7238131 A | 9/1995 |
| JP | 2004-131707 | 4/2004 |
| JP | 7238207 A | 9/2005 |
| WO | 93/10734 A1 | 6/1993 |
| WO | 00/14170 A | 3/2000 |
| WO | 02/057386 A2 | 7/2002 |

OTHER PUBLICATIONS

Handbook of Pressure Sensitive Adhesive Technology, Chp. 13, Don Sates, Thermoplastic Rubbers A-B-A Block Copolymers, p. 367 (1989, 2nd Ed.).
Taiwan Patent Application No. 993104284, filed Feb. 20, 2004, Translation of Office Action dated Oct. 1, 2007.
Chinese Patent Application No. 200480008803.6, filed Feb. 19, 2004, Translation of Second Office Action dated Mar. 9, 2007.
Chinese Patent Application No. 200480008803.6, filed Feb. 19, 2004, Translation of Decision of Chinese Office Action dated Mar. 7, 2008.
Japanese Patent Application No. 2006-500117, filed Feb. 19, 2004, Translation of Office Action dated Aug. 4, 2009.

*Primary Examiner*—Thao T. Tran
(74) *Attorney, Agent, or Firm*—Novak, Druce & Quigg LLP

(57) ABSTRACT

Adhesive composition for tapes, labels and bandages to be used at temperatures of +5° C. and lower, comprising (a) at least one block copolymer, comprising at least two terminal blocks of poly(vinyl aromatic compound) and at least one midblock of a randomly copolymerized mixture of isoprene and butadiene, optionally mixed with a diblock copolymer comprising one poly(vinyl aromatic compound) block and one randomly copolymerized mixbjre of isoprene and butadiene, and optionally mixed with a block copolymer, comprising at least one block of poly(vinyl aromatic compound) and at least one block of poly(butadiene) or poly(isoprene), (b) at least one mixed aliphaticlaromatic tackifying resin or a blend of aliphatic and aromatic tackifying resins, having an aromatic H-NIVIR content between 6 and 22%, and (c) a plasticizer in an amount of at most 25 wt %, relative to the weight of the adhesive composition; and tapes, labels and bandages comprising said adhesive compositions, applied on a substrate layer; and the use of said tapes, labels or bandages.

11 Claims, No Drawings

ADHESIVE COMPOSITION AND TAPES AND LABELS DERIVED THEREFROM

BACKGROUND ART

Adhesive compositions based on styrenic block copolymers as thermoplastic elastomer components are well known in the art. These compositions are for instance used in pressure sensitive adhesive (PSA) for industrial tapes, packaging tapes, labels and bandages (e.g. plasters).

More in particular styrene-isoprene-styrene block copolymers (S-I-S) and styrene-butadiene-styrene block copolymers (S-B-S) are widely used in these adhesive compositions. Both classes of block copolymers give the adhesive compositions specific properties related to the respective inherent characteristics of these block copolymers.

For example, the softness of S-I-S makes this polymer type the material of choice for pressure sensitive applications in tapes and labels, while the elevated cohesion of S-B-S makes this material attractive for construction adhesives for disposable soft goods.

S-I-S block copolymers have until now successfully been applied in industrial and packaging tape and label applications.

More in particular, from e.g. U.S. Pat. No. 5,389,438 (MINNESOTA MINING MFG) 02.12.1995; EP 306232 A (MINNESOTA MINING MFG) 08.03.1989; EP 443263 A (MINNESOTA MINING MFG) 28.08.1991; WO 0014170 (EXXON) 16.03.2000 and U.S. Pat. No. 6,384,138 (EXXON) 07.05.2002 adhesive compositions to be used for tapes, labels, bandages or disposable sanitary articles, such as diapers and incontinence garments, were known. Said adhesive compositions comprised:
1. at least one block copolymer, comprising at least two terminal blocks of poly(vinyl aromatic compound) and at least one midblock of poly(isoprene) or poly(butadiene) or poly(ethylene-butylene), i.e. hydrogenated poly(butadiene, or a mixture of said block copolymers,
2. at least one tackifying resin, and
3. a plasticizer.

It will be appreciated that in none of said publications any reference is made to the use of the adhesive compositions at low temperatures, i.e. below room temperature.

Although in particular S-I-S block copolymer containing compositions showed outstanding tack, peel and cohesion at room temperature, i.e. at temperatures around 20° C., they have appeared to lack adequate adhesive properties in cold environments, namely 5° C. and below.

It is well known from e.g. Handbook of Pressure Sensitive Adhesive Technology, Don Satas, Chapter 13, Thermoplastic Rubbers, A-B-A block copolymers, p 367 (1989, $2^{nd}$ ed.), that most adhesive compositions based on S-I-S block copolymers loose their tack and adhesion properties as temperature decreases from about 15° C.

It was possible to formulate adhesive compositions based on S-I-S block copolymers, having a good tack below 15° C., but in order to achieve an acceptable compromise with the adhesive properties, relatively low proportions of high softening point hydrocarbon resins and relatively high proportions of plasticizers are needed.

However, high proportions of plasticizer have the disadvantages (a) that the peel and cohesion of the adhesive is reduced and (b) that the plasticizer migrates out of the formulation, modifying the visual and property appearance of the final products, like oily spots in a paper label.

During the splitting of roll products, too much oil generates edge oozing, provoking that two adjacent rolls stick together.

Therefore there is a strong need for adhesive compositions which keep good tack, adhesion and cohesion at low temperatures, and more in particular at temperatures in the range from +5 to −25° C., which enables the manufacture of tapes and labels to be used in cold environments e.g. some electrical insulating tapes or on frozen articles, e.g. food and medicines in deep freezers.

It is an object of the present invention to provide adhesive compositions which keep good tack, adhesion and cohesion at low temperatures, and which do not contain high amounts of plasticizers.

Another object of the present invention is formed by labels and tapes which retain adequate properties when stored for a long time at low temperatures.

Another object of the present invention is to provide adhesive compositions which enable the manufacture of repositionable or removable tapes, labels and bandages (e.g. plasters) which can be used at low temperatures.

As result of extensive research and experimentation, said adhesive compositions aimed at, and labels, tapes and bandages to be manufactured from them, have now surprisingly been found.

DISCLOSURE OF THE INVENTION

Accordingly the present invention relates to an adhesive composition for tapes, labels and bandages to be used at temperatures of +5° C. and lower, comprising (a) at least one block copolymer, comprising at least two terminal blocks of poly(vinyl aromatic compound) and at least one midblock of a randomly copolymerized mixture of isoprene and butadiene, said block copolymer being optionally mixed with a diblock copolymer, comprising one poly(vinylaromatic) block and one randomly copolymerized mixture of isoprene and butadiene, and optionally mixed with a block copolymer, comprising at least one block of poly(vinyl aromatic compound) and at least one block of poly(butadiene) or poly(isoprene), (b) at least one mixed aliphatic/aromatic tackifying resin or a blend of aliphatic and aromatic tackifying resins, having an aromatic H-NMR content between 6 and 22%, and (c) a plasticizer in an amount of at most 25 wt %, relative to the weight of the adhesive composition, and to tapes, labels and bandages derived from it.

MODE(S) FOR CARRYING OUT THE INVENTION

Component (a)

The main block copolymer component used in the adhesive composition is a block copolymer, having a structure represented by the general formulae S-(I/B)-S (1) or $[S-(I/B)]_nX$ (2), optionally mixed with a diblock copolymer S-(I/B), and optionally mixed with minor amounts of one or more block copolymers, selected from the group S-B, S-B-S, S-I and S-I-S, wherein S represents a poly(vinyl aromatic compound) block, (I/B) represents a block of a randomly copolymerized mixture of isoprene and butadiene, wherein the weight ratio between isoprene and butadiene is in the range of from 70:30 to 30:70, or in a mole/mole ratio of from 1.1/0.55 to 0.45/1.3, wherein B represents a poly(butadiene) block wherein I represents a poly(isoprene) block, wherein n is an integer equal to or greater than 2, and wherein X is the residue of a coupling agent.

Preferred weight ratios between isoprene and butadiene are in the range of from 60:40 to 30:70 or in a molar ratio of from 0.89/0.75 to 0.45/1.3.

As an example of the aromatic vinyl compound useful in the practice of the present invention, may be mentioned styrene, alpha-methylstyrene, p-methylstyrene, o-methylstyrene, p-tert.butylstyrene, dimethylstyrene, and vinyl naphthalene or mixtures thereof. Of these, styrene is particularly preferred from the viewpoints of easy availability, reactivity, physical properties of the resulting block copolymers. The A polymer block may contain minor amounts of comonomers other than an aromatic vinyl compound, e.g., up to 5 wt % of a copolymerizable monomer such as butadiene and/or isoprene (based on the weight of the total block). Most preferred are A blocks derived from substantially pure styrene.

These polymer blocks A preferably have a true molecular weight in the range from 9,500 to 25,000.

The mixed polymer midblock (I/B) is made of butadiene and isoprene as copolymerizing monomers, although it too may contain minor amounts of other comonomers, e.g. up to 5 wt % of a copolymerizable monomer such as styrene (based on the weight of the total block), but mixtures of substantially pure isoprene and butadiene are preferred.

In the block copolymers according to the present invention, the proportion of bound aromatic vinyl compound is in the range of 10-50 wt %, preferably 15 wt % based on the total block copolymer. The proportion of bound butadiene is 18-80 wt %, preferably 40-70 wt % in total. The proportion of bound isoprene is 15-70 wt %, preferably 30-70 wt %. These amounts of bound monomers (plus copolymerizable monomers, if any) add up to 100 wt %.

The block copolymers to be applied in the adhesive compositions according to the present invention each preferably have a weight average molecular weight (Mw, expressed in terms of polystyrene) ranging from 100,000 to 500,000, preferably from 150,000 to 250,000 as determined by gel permeation chromatography (GPC, analogous to the method described in ASTM D5296-97).

The block copolymers to be applied in the adhesive compositions according to the present invention each preferably contain 1,2-vinyl bonds and/or 3,4-vinyl bonds in a proportion in the range of from 5 to 40 wt % based on the weight of the conjugated diene or in the range of from 0.08 to 0.70 mole/mole %, and preferably from 5 to 20 wt %, based on the weight of conjugated diene or 0.08 to 0.35 mole/mole %. The block copolymers according to the present invention preferably each have a storage modulus (G') of 1 to 300 MPa in a visco-elasticity measurement in a temperature range of from 0 to 50° C., and only one peak on loss tangent (tan δ) attributable to the mixed butadiene/isoprene polymer block at a temperature of −50° C. or below. When a block copolymer having a storage modulus (G') lower than 1 MPa is used as a base polymer for a pressure sensitive adhesive, then the holding power of the PSA is lowered. On the other hand, any storage modulus exceeding 300 MPa results in a pressure sensitive adhesive lowered in tackiness.

Said block copolymers to be applied as main component (a) in the adhesive composition, have a randomly copolymerized block (I/B), which means that the mixed midblock shows no significant single homopolymer block formation.

They can be prepared as described in WO 02057386 (KRATON) 25.07.2002, which is herein incorporated by reference.

More in particular, polymers having mixed midblocks may be defined as having average homopolymer block lengths of less than 100 monomer units, preferably less than 50 monomer units, more preferably less than 20 monomer units.

Average homopolymer block length may be determined by carbon-13 NMR, as described in detail in WO 02057386.

The block copolymers according to the present invention can be made e.g. by coupling living diblock copolymer prepared by anionic polymerization with a coupling agent.

As examples of the coupling agent may be mentioned tin coupling agents such as tin dichloride, monomethylin dichloride, dimethyitin dichloride, monoethyltin dichloride, diethyltin dichloride, methyltin trichloride, monobutyltin dichloride, dibutyltin dibromide, monohexyltin dichloride and tin tetrachloride; halogenated silicon coupling agents such as dichlorosilane, monomethyldichlorosilane, dimethyldichlorosilane, monoethyldichlorosilane, diethyldichlorosilane, monobutyldichlorosilane, dibutyldichlorosilane, monohexyldichlorosilane, dihexyldichlorosilane, dibromosilane, monomethyldibromosilane, dimethyldibromosilane, silicon tetrachloride and silicon tetrabromide; alkoxysilanes such as tetramethoxysilane; divinyl aromatic compounds such as divinylbenzene and divinylnaphthalene; halogenated alkanes such as dichloroethane, dibromoethane, methylene chloride, dibromomethane, dichloropropane, dibromopropane, chloroform, trichloroethane, trichloropropane and tribromopropane; halogenated aromatic compounds such as dibromobenzene; epoxy compounds such as the diglycidyl ether of bisphenol-A and the like (e.g., EPON™ 825 or EPON™ 826 diglycidyl ether) and other coupling agents such as benzoic esters, CO, 2 and 1-chloro-1,3-butadiene. Of these, EPON™ 826 diglycidyl ether, dibromobenzene, tetramethoxysilane or other tetra(alkoxy)silanes are preferred.

The main block copolymer in component (a) may hence comprise a mixture of the coupled polymer according to the general formulae (1) or (2) and of the intermediate diblock, e.g. in a weight ratio of 100/0 to 30/70.

It will be appreciated that the main block copolymer component (a) may also be formed by a block copolymer obtained by sequential polymerization of batches of the respective monomers (e.g. styrene and mixtures of butadiene/isoprene, optionally in combination with reinitiation, if additional diblock copolymer is desired.

The block copolymers of formulae (1) and (2) can be made by mere adaptation of common processes used for the preparation of S-B-S type block copolymers and/or S-I-S type block copolymers, using a mixture of butadiene/isoprene instead. Of importance in the preparation of the block copolymers according to the present invention is to avoid homopolymer block formation, to ensure appropriate B/I ratio, and to produce a polymer block wherein the random midblock has a Tg of −50° C. or less. Generally no randomizer will be used.

As specified hereinbefore, the main block copolymer of formulae (1) or (2), which usually will comprise corresponding diblocks, can be mixed with minor proportions of conventional diblock copolymers and/or triblock copolymers, comprising poly(vinyl aromatic compound) blocks and poly(butadiene) blocks or poly(isoprene) blocks in a proportion of from 0 to 50 wt %, relative to the weight of component (a) and preferably in a proportion of from 0 to 30 wt %.

More preferably said diblock copolymers and triblock copolymers have been obtained in one process, comprising the preparation of an initial living diblock, which can be subsequently coupled to a triblock copolymer by means of a coupling agent as specified hereinbefore.

It will be appreciated that the diblock copolymer and/or triblock copolymers, which can optionally be incorporated in component (a), may have apparent molecular weights which are about the half of those of the main block copolymer component for an additional copolymer diblock and about the same as those of the main block copolymer for an additional triblock copolymer respectively.

Component (b)

Suitable tackifying resins or mixtures of resins have been found to have an aromatic H-NMR content between 6 and 22%, and preferably from 9 to 22%, and more preferably from 9 to 18%. More preferred tackifying resins show a differential scanning calorimetry (DSC) glass transition temperature Tg between 30° C. and 40° C., and preferably between 35 and 38° C., and a Ring and Ball softening point between 80° C. and 90° C.

They can be selected from modified aliphatic hydrocarbon resins such as modified C5 hydrocarbon resins (C5/C9 resins), styrenated terpene resins, partially hydrogenated C9 hydrocarbon resins and mixtures thereof. The aromatic component may be a feedstream composed by one or more of the following chemicals like polystyrene, alpha-methyl styrene, vinyl toluene, alkyl substituted indenes and related homologues.

More preferred examples of resins to be used as component (b) are: MBG 223, a modified aliphatic hydrocarbon resin, showing a H-NMR aromatic content of 11.3%, a Ring and Ball softening point of 88° C., manufactured by Eastman B.V. and WINGTACK™ 86, a modified hydrocarbon resin, showing a H-NMR aromatic content of 9.6% and a Ring and Ball softening point of 86° C., manufactured by GOODYEAR CHEMICALS. Preferred solid tackifying resins will have Ring and Ball softening points in the range of from 85 to 90° C.

The adhesive composition according to the present invention preferably comprises from 50 to 300 parts by weight and more preferably from 100 to 200 parts by weight of tackifying resin per 100 parts by weight of component (a).

In preferred adhesive compositions, the component (b) occurs in a proportion of from 35 to 55 wt %, relative to the weight of the composition.

Component (c)

Suitable plasticizers include predominantly plasticizing oils that are paraffinic or naphthenic in character (carbon aromatic distribution $\leq 5\%$, preferably $\leq 2\%$, more preferably 0% as determined according to DIN 51378) and a glass transition temperature lower than $-55°$ C. as measured by Differential Scanning Calorimetry. Those products are commercially available from the Royal Dutch/Shell Group of companies, like SHELLFLEX™, EDELEX™, and ONDINA™ oils. Other oils include KAYDOL™ oil from Witco, or TUFFLO™ oils from Arco or NYPLAST™ from NYNAS. Other plasticizers include compatible liquid tackifying resins like REGALREZ™ R-1018 or WINGTACK™ 10.

Other plasticizers may also be added, like olefin oligomers; low molecular weight polymers ($\leq 30,000$ g/mol) like liquid polybutene, liquid polyisoprene copolymers, liquid styrene/isoprene copolymers or liquid hydrogenated styrene/conjugated diene copolymers; vegetable oils and their derivatives; or paraffin and microcrystalline waxes.

The composition according to the present invention preferably comprises a plasticizer in a weight proportion of from 5 to 15 wt %, relative to the weight of the complete composition and of from 10 to 85 parts by weight of plasticizer per 100 parts by weight of block copolymer constituent (a). Also each block copolymer of component (a) may be pro-blended with a small amount of plasticizer by the manufacturer of said copolymer.

Other Components (Non-Limitative)

Other rubber components may be incorporated into the adhesive compositions according to the present invention. It is also known in the art that various other components can be added to modify the tack, the odour, the colour of the adhesives. Antioxidants and other stabilizing ingredients can also be added to protect the adhesive from degradation induced by heat, light and processing or during storage.

Several types of antioxidants can be used, either primary antioxidants like hindered phenols or secondary antioxidants like phosphite derivatives or blends thereof. Examples of commercially available antioxidants are IRGANOX™ 565 from Ciba-Geigy (2,4-bis-(n-octylthio)-6-(4-hydroxy-3,5-di-tertiary-butyl anilino)-1,3,5-triazine), IRGANOX 1010 from Ciba-Geigy (tetrakis-ethylene-(3,5-di-tertiary-butyl-4-hydroxy-hydrocinnamate)methane) and POLYGARD™ HR from Uniroyal (tris-(2,4-di-tertiary-butyl-phenyl)phosphite). Other antioxidants developed to protect the gelling of the polybutadiene segments can also be use, like the SUMILIZER™ GS from Sumitomo (2[1-(2-hydroxy-3,5-di-ter-pentylphenyl)ethyl)]4,6-di-tert-pentylphenylacrylate); SUMILIZER T-PD from Sumitomo (pentaerythrythyltetrakis(3-dodecylthiopropionate)); or mixtures thereof.

Preparation of the Composition

No particular limitation is imposed on the preparation process of the adhesive composition. Therefore, there may be used any process such as a mechanically mixing process making use of rolls, a Banbury mixer or a Dalton kneader, a hot-melt process characterized in that heating and mixing are conducted by using a meting kettle equipped with a stirrer, like a high shear Z-blade mixer or a single- or twin-screw extruder, or a solvent process in which the compounding components are poured in a suitable solvent and stirred, thereby obtaining an intimate solution of the pressure sensitive adhesive composition.

Use of the Composition

PSA compositions according to the present invention may be applied without using any solvent (e.g., hot-melt) or in the form of their solutions to a base material such as paper or a plastic film by means of a proper coater, thereby producing various kinds of pressure sensitive adhesive tapes for tapes or labels which can be used in cold environments and which can be used for long storage at low temperatures.

During label manufacture, a laminate of a face stock, pressure sensitive adhesive layer and a release liner are passed through an apparatus which converts the laminate into commercially useful labels and label stock. The process involves, amongst others, die-cutting and matrix stripping to leave labels on a release liner.

It has surprisingly been found that during the manufacture of tapes, labels and bandages according to the present invention, the fouling of knives used in sitting and cutting of roll and sheet stocks is significantly reduced.

It will be appreciated that another aspect of the present invention is formed by the use of tapes, labels or bandages on packed frozen articles such as food, medicines and the like. A more particular aspect is formed by the use of repositionable or removable tapes or labels on frozen articles.

The present invention will hereinafter be illustrated more specifically by the following examples, however without restricting the scope to these specific embodiments.

Test Methods

Standard peel, tack, cohesion and viscosity tests were carried out on these formulations as described in the Test method manual for Pressure Sensitive Tapes from the Pressure Sensitive Tape Council (PSTC), the standard FINAT test method for Pressure sensitive materials, the AFERA test methods for Pressure Sensitive Adhesive Tapes and the ASTM related methods. Different testing surfaces have been used in function of the application: chromed stainless steel plates (No. 304) ("ss") as recommended by the FINAT and Kraft paper.

Rolling Ball Tack (RBT) is the distance expressed in centimetres; a steel ball rolls on the adhesive film with a standard initial velocity (Pressure Sensitive Tape Council Test No. 6; ASTM 03121-73). Small numbers indicate aggressive tack.

Loop Tack (LT) was determined using PSTC5 and FTM 9 loop tack method. High numbers LT indicate aggressive tack. Results are expressed in Newton/25 mm (N/25 mm).

Peel Adhesion (PA) was determined by Pressure Sensitive Tape Council Method No. 1 and ASTM D3330-83. Large numbers Indicate high strength when peeling a test tape from a steel substrate. Results are expressed in N/25 mm.

Holding Power (HP) is the time required to pull a standard area (2.5×1.3 cm) of tape from a standard test surface (steel=ss) under a standard load (1 kg, 2 or 5 kg), in shear at 2° (Pressure Sensitive Tape Council Method No. 7; ASTMD-3654-82). Long times indicate high adhesive strength. Results are expressed in hours (h) or minutes (min). The type of failure mode is expressed as adhesive failure (AF) or cohesive failure (CF). This test can be carried out at room temperature (about 23° C.) or at a more elevated temperature, depending on the test.

The SHAFT (shear adhesion failure temperature) was measured by 2.5×2.5 cm Mylar to chromed ss plates with a 1 kg weight. The samples are placed in an oven and the temperature is raised by 22° C./minute. SAFT measures the temperature at which the lap shear assembly fails.

Glass transition temperatures Tg have been determined by Differential Scanning calorimetry with a temperature sweep of 40° C./min. The Tg is measured at the onset of the transition.

Polystyrene content was determined by 1H-NMR.

Average homopolymer block lengths have been determined by $^{13}C$ NMR using the method described herein before. $^{13}C$ NMR spectra of polymer samples were obtained with a Bruker AMX-500 FT spectrometer operating at 125 MHz. Quantitative proton-decoupled spectra were recorded with a 90° $^{13}C$ excitation pulse and a repetition rate of 10 s. 10% (w/w) of polymer solutions in $CDCl_3$ were used. To improve the relaxation time 0.1 mol/l chromium acetylacetonate was added. The applied line broadening was 2 Hz. The spectra were referenced such that the aliphatic carbons of trans-polybutadiene are at 31.9 ppm.

Quantification of the percentage (%) of aromatic proton in aromatic modified hydrocarbon resin was done by liquid 1H-NMR after dissolving the samples in deuterated chloroform and measuring with a BRUKER DPX-300.

Ring and Ball softening point is a measure of the temperature at which a resin softens following the ASTM E-28 test method.

Low temperature conditions: the tack tests have been carried out in a climate chamber, wherein the temperature could be adjusted down to 0° C. The RBT has been measured at respectively 23, 15, 10, 5 and 0° C. Prior to testing the samples have been conditioned at the testing temperature during 24 hours.

Synthesis of the Block Copolymers A and B

Cyclohexane, styrene, butadiene and isoprene were purified by activated aluminumoxide and stored at 4° C. under a nitrogen atmosphere. EPON 826 diglycidyl ether and dibromoethane (EDB) were used as coupling agent. Prior to synthesis, a monomer mixture of butadiene and isoprene (at a weight/weight ratio given in Table 1) was prepared and stored under nitrogen at 4° C. This mixture was used as such.

An autoclave, equipped with a helical stirrer was charged with cyclohexane and the content was heated to 50 to 60° C. As initiator sec-BuLi was dosed immediately followed by styrene monomer, which was allowed to polymerize to completion. The reaction temperature was increased to 70° C., at which temperature a butadiene/isoprene monomer mixture (B/I) was dosed and reacted. The resulting diblock was coupled with an excess EPON 826 diglycidyl ether or alternatively with an excess of EDB. This excess was optionally scavenged with sec-BuLi and followed by addition of ethanol as terminator. The reaction mixture was cooled to 40° C., transported to a blending vessel and a stabilization package was added (comprising IRGANOX 565 and tris(nonylphenol)phosphite 0.08/0.35 phr as a cyclohexane solution) and stirred at RT. Dry rubber was obtained by steam coagulation finishing, followed by drying in an oven.

The polymers were analyzed by GPC. Table 1 lists the amounts in which the components have been used. The results of the GPC analysis are in Table 2. Further components used in the examples are listed in Table 3.

Synthesis of Polymer with Sequential/Reinitiation (Polymer C)

Cyclohexane, styrene, butadiene and isoprene have been purified by activated aluminumoxide and were stored at 4° C. under a nitrogen atmosphere.

Prior to synthesis, a monomer mixture of butadiene and isoprene (at the desired weight/weight ratio) was prepared and stored under nitrogen at 4° C. This mixture was used as such. An autoclave, equipped with a helical stirrer was charged with cyclohexane and the content was heated to 50° C. As initiator sec-BuLi was dosed immediately followed by styrene monomer that was allowed to polymerize to completion. The reaction temperature was increased to 60° C. and followed by dosing and reaction to completion of a butadiene/isoprene monomer mixture (B/I). A second portion of sec-BuLi was dosed immediately followed by dosing and reacting to completion of a butadiene/isoprene monomer mixture (B/I). A second portion of styrene monomer was dosed and reacted to completion. The reaction mixture was terminated with a stoichiometric amount of alcohol, cooled to 40° C., transported to a blending vessel and a stabilization package was added and stirred at room temperature. White polymer was obtained by steam coagulation finishing, followed by drying in an oven.

The polymer was analyzed by GPC. The results have been listed in Table 2.

TABLE 1

|  | Polymer | | |
| --- | --- | --- | --- |
|  | A | B | C |
| Cyclohexane (l) | 77 | 14 | 30 |
| Initiator (mmol) | 20.5 | 27.4 | 28 |
| Styrene (gram) | 300 | 329 | 290 |
| B/I (ratio) | 1.5 | 1 | 1 |
| B/I (gram) | 1490 | 1637 | 1230 |
| Initiator (mmol) |  |  | 23.5 |

TABLE 1-continued

|  | Polymer | | |
| --- | --- | --- | --- |
|  | A | B | C |
| B/I (gram) |  |  | 2285 |
| EPON 826 (gram) | 0.24 |  |  |
| EDB (ml) |  | 0.56 |  |
| Ethanol (ml) | 1 | 1 | 1 |

TABLE 2

|  | Polymer | | |
| --- | --- | --- | --- |
|  | A | B | C |
| Mw Polystyrene *$10^3$ | 10.8 | 10.9 | 10.9 |
| Total Mw *$10^3$ | 188 | 245 | 191 |
| Coupling efficiency % | 71 | 43 | 68 |
| Polystyrene content wt % | 18 | 17 | 19 |
| B/I ratio | 40/60 | 50/50 | 50/50 |
| Vinyl in B wt % | 8 | 8 | 8 |
| Vinyl in I wt % | 5 | 5 | 5 |

Further components used in the tested adhesive compositions have been listed in Table 3.

TABLE 3

KRATON D-1160 is a linear styrene-isoprene-styrene block copolymer with 19% polystyrene content, a total molecular weight of 178,000 g/mole and a coupling efficiency of 100%
KRATON D-1113 is a linear styrene-isoprene-styrene block copolymer with 16% of polystyrene content, a coupling efficiency of 44% and a total molecular weight of 240,000 g/mole
Polymer A is a linear styrene-isoprene/butadiene-styrene block copolymer with 18% polystyrene content, a coupling efficiency of 71%, a weight average total molecular weight of 188,000 g/mole and a isoprene/butadiene w % ratio of 60/40
Polymer B is a linear styrene-isoprene/butadiene-styrene block copolymer with 17% of polystyrene content, a coupling efficiency of 43%, a weight average total molecular weight of 245,000 g/mole and an isoprene/butadiene wt % ratio of 50/50
Polymer C is a linear styrene-(isoprene/butadiene)-styrene block copolymer with a 19 wt % polystyrene content, a weight average total molecular weight of 191 000 g/mole and a isoprene/butadiene wt % ratio of 50/50, mixed with a styrene-(isoprene/butadiene) diblock copolymer with a molecular weight of 95,000 g/mole, and a proportion of 30 mol/mole %, relative to the triblock copolymer
KRATON D-1118 is a linear styrene-butadiene-styrene block copolymer with 31% of polystyrene content, a coupling efficiency of 22% and a total molecular weight of 170,000 g/mole
FINAPRENE 1205 is a styrene-butadiene diblock copolymer with a polystyrene content of 25%, having a total molecular weight of 120,500 g/mole
PICCOTAC 1094 is an aliphatic hydrocarbon resin with a Ring and Ball softening point of 95° C., a NMR-H aromaticity of 0%, developed by EASTMAN BV
MBG 223 is an experimental aliphatic/aromatic hydrocarbon resin with a Ring and Ball softening point of 88° C., a NMR-H aromaticity of 11.3%, a glass transition temperature Tg of 36° C. developed by EASTMAN BV
WINGTACK 86 is an aliphatic/aromatic hydrocarbon resin with a Ring and Ball softening point of 86° C. and a NMR-H aromaticity of 9.6%, a glass transition temperature Tg of 37° C. developed by GOODYEAR CHEMICALS
QUINTONE S-100 is an aliphatic/aromatic hydrocarbon resin with a Ring and Ball softening point of 94° C. a NMR-H aromaticity of 6.3%, a glass transition temperature Tg of 49° C. developed by ZEON
WINGTACK ET is an aliphatic/aromatic hydrocarbon resin with a Ring and Ball softening point of 94° C. a NMR-H aromaticity of 4.2%, a glass transition temperature Tg of 44° C. developed by GOODYEAR CHEMICALS
PICCOTAC 6085 is an aliphatic/aromatic hydrocarbon resin with a Ring and Ball softening point of 98° C. a NMR-H aromaticity TABLE 3-continued of 13.5%, a glass transition temperature Tg of 43° C. developed by EASTMAN
ECR 373 is an aliphatic/aromatic hydrocarbon resin with a Ring and Ball softening point of 86° C. a NMR-H aromaticity of 11.75%, a glass transition temperature Tg of 41° C. developed by EXXON MOBIL Chemicals
MBG 222 is an experimental aliphatic/aromatic hydrocarbon resin with a Ring and Ball softening point of 85° C. a NMR-H aromaticity of 4%, a glass transition temperature Tg of 34° C. developed by EASTMAN
EDELEX 956 is a naphtenic oil from DEUTSCHE SHELL AG.
EDELEX SM 925 is a paraffinic oil from DEUTSCHE SHELL AG
IRGANOX is an anti-oxidant from CIBA All the formulations in the examples have been prepared out of solvent. The different ingredients were poured in toluene and mixed for 24 hours to obtain the dissolution. Afterward, the solutions have been coated on a Polyester Film (Mylar −36 microns thick) with an automatic Bar Coater to obtain an adhesive coating weight of 22 g/m$^2$ dry. Thereafter, the samples have been laminated with a siliconised paper to protect them. Prior to testing, the samples are stored in a conditioned room at 21° C. and 50% relative humidity.

EXAMPLE 1

The adhesive properties of formulations based on a SIS and the polymer A and C (described in Table 1) are compared in Table 4. Particularly, the Rolling Ball Tack has been measured at different temperatures, as low as +5° C. in this case.

It is clearly demonstrated that the combination of polymer A and the WINGTACK 86 allows to have good tack properties at low temperature, much better than SIS in the same formulation.

TABLE 4

| Ingredients | units | F-1 Comp | F-2 | F-3 |
| --- | --- | --- | --- | --- |
| KRATON D-1160 | phr | 100 |  |  |
| Polymer A | phr |  | 100 |  |
| Polymer C | phr |  |  | 100 |
| WINGTACK 86 | phr | 110 | 110 | 110 |
| EDELEX 956 N | phr | 10 | 10 | 10 |
| IRGANOX 1010 | phr | 3 | 3 | 3 |
| RTB at +23° C. | cm | 12 | 1.6 | 4 |
| RTB at +15° C. | cm | >40 | 3.4 | 9.5 |
| RTB at +10° C. | cm | — | 4 | 25 |
| RTB at +5° C. | cm | — | 23 |  |
| Loop Tack 23° C. | N/25 mm | 15 | 15 | 16 |
| Peel Adhesion 23° C. | N/25 mm | 18 | 12 | 13 |
| Holding Power 2 kg/23° C. | hours | >100 | 50 | >100 |

EXAMPLE 2

The adhesive properties of formulations based on SIS and polymer B (described in Table 1) are presented in Table 5.

The glass transition temperatures are calculated with the help of the Fox Equation (Handbook of Pressure Sensitive Adhesive Technology—Don Satas—1989—page 369). The Rolling Ball Tack has been measured at different decreasing temperatures down to 0° C.

At the same ingredient ratio and same formulation composition (Formulations F-4 and Formulation F-6), the polymer B allows to achieve better tack at lower temperature than the SIS formulation. If the composition of the SIS formulation (F-4) is adjusted to have the same formulation glass transition temperature Tg of −25° C. as that of the F-6 containing the polymer B, then the Formulation F-5 is obtained that contains a higher level of oil, namely 85 phr versus of 40.

This higher amount of oil in Formulation F-5 improved the Rolling Ball Tack values but has the following detrimental effects:

- the other adhesive properties tack, peel adhesion, cohesion and SAFT (Shear Adhesive Failure temperature) are much lower and therefore the adhesive properties are not well balanced;
- the higher oil content will enhance the oil bleeding in the front material, like paper in labels, creating undesirable side effects (oily spots that reduces the aesthetics of the paper surface) and modification of the adhesive properties;
- the higher oil content is also the responsible for the edge oozing of the adhesive because of the lower cohesion, and provokes the mutual sticking of adjacent tape rolls and that of stacked sheets.

Therefore, the polymers of the invention are well designed to develop adhesives with lower service temperature than SIS but with the marked advantage to use less oil or plasticizer.

TABLE 5

|  | units | CompF-4 | CompF-5 | F-6 |
|---|---|---|---|---|
| D-1113 | phr | 100 | 100 |  |
| Polymer B | phr |  |  | 100 |
| WINGTACK 86 | phr | 140 | 140 | 140 |
| EDELEX 956 | phr | 40 | 85 | 40 |
| IRGANOX 1010 | phr | 3 | 3 | 3 |
| calculated Tg | °C. | −18 | −25 | −25 |
| RBT at +23° C. | cm | 2 | 1.2 | 1 |
| RBT at +15° C. | cm | 3.5 | 1.7 | 2 |
| RBT at +10° C. | cm | >40 | 2.3 | 3.5 |
| RBT at +5° C. | cm |  | 6.3 | 19.5 |
| RBT at 0° C. | cm |  | >30 | >30 |
| LT | N/25 mm | 17 | 12 | 15 |
| PA | N/25 mm | 15 | 8 | 14 |
| HP ss 1 kg | min | 660 | 216 | 1560 |
| HP ss 2 kg | min | 240 | 48 | 190 |
| SAFT | °C. | 80 | 75 | 85 |

EXAMPLE 3

In label adhesives, SIS polymers are often blended with SB or SBS block copolymers to make the formulation softer and better suited for the label converting, namely the die-cutting and matrix stripping processes (U.S. Pat. No. 5,663,228 (AVERY DENNISON) 02.09.1997). However, it should be noticed that blends of polymers of the present invention, like Polymer A, B and C with SIS, SBS and SB are miscible and give only one tan delta peak as measured by Dynamic mechanical analysis.

Table 6 shows the Pressure Sensitive Adhesive results obtained for SIS/SB and Polymer B/SB and SBS. Results from Formulations F-7/F-8 show that an aliphatic resin is not good for a Polymer B/SB blend (F-8) as there is no tack measured neither by the Rolling ball Tack nor by the Loop Tack.

The combination of Polymer B/SB with MBG 223 (F-9) and WINGTACK 86 (F-10) provide to the formulations good tack properties at lower temperature than SIS. It is also seen in Formulation F-11 compounded that with a paraffinic oil, having a lower glass transition temperature Tg than the naphtenic oil, that the Rolling ball tack values are excellent even at temperature as low as 0° C.

Properties obtained with blends of Polymer B/SB (F-11) and Polymer B/SRS (F-12) are similar with slightly better cohesion with the formulation F-12 because SBS is a triblock copolymer. It should also be pointed out that the adhesive of Formulation F-11 has the characteristics of being a good removable adhesive. Applied on a paper surface, this adhesive can be easily removed even after a prolonged storage period.

TABLE 6

| Ingredients | Units | F-7 | F-8 | F-9 | F-10 | F-11 | F12 comp |
|---|---|---|---|---|---|---|---|
| D-1113 | phr | 44 |  |  |  |  |  |
| Polymer B | phr |  | 44 | 44 | 44 | 44 | 44 |
| SOLPRENE 1205 | phr | 56 | 56 | 56 | 56 | 56 |  |
| KRATON D-1118 | phr |  |  |  |  |  | 56 |
| PICCOTAC 1094 | phr | 100 | 100 |  |  |  |  |
| MBG 223 | phr |  |  | 100 |  |  |  |
| WINGTACK 86 | phr |  |  |  | 100 | 100 | 100 |
| EDELEX 956 | phr | 63 | 63 | 63 | 63 |  |  |
| EDELEX 925 | phr |  |  |  |  | 63 | 63 |
| IRGANOX 1010 | phr | 3 | 3 | 3 | 3 | 3 | 3 |
| RBT at +23° C. | cm | 5 | >40 | 2 | 1.6 | 1.5 | 1.7 |
| RBT at +15° C. | cm | 21 |  | 3 | 2 | 2.2 | 2 |
| RBT at +10° C. | cm | >40 |  | 8 | 1.7 | 2 | 2.3 |
| RBT at +5° C. | cm |  |  | 8 | 2 | 2.1 | 2.3 |
| RBT at 0° C. | cm |  |  | n.m | >30 | 7 | 9 |
| Loop tack | N/25 mm | 16 | 0 | 15 | 11 | 7 | 6 |
| Peel Adhesion | N/25 mm | 13 | 16 | 15 | 13 | 5.6 | 6 |
| HP 2 kg | hours | 0.3 | 0.4 | 0.5 | 12 | 6 | 18 | n.m = not measured

EXAMPLE 4

The rolling Ball Tack values in function of the temperature for several adhesive formulations based on different hydrocarbon resins are shown in Table 7. The formulations tested were polymer/hydrocarbon resin/oil/anti-oxidant in a ratio 100/110/15/3, based on parts per hundred of rubber (phr). Formulation F-17 and F-18 have better low temperature RBT values because both WINGTACK 86 and MBG223 have the appropriate balance of glass transition temperature Tg, NMR-H aromaticity and R&B Softening points.

In the Table, the following abbreviations are used:

QUINTONE S100; WINGTACK ET; PICCOTAC 6095; ECR 373; WINGTACK 86; MBG 223; MBG 222.

TABLE 7

| Ingredients | Units | F-13 | F-14 | F-15 | F-16 | F-17 | F-18 | F19 |
|---|---|---|---|---|---|---|---|---|
| Type of resin |  | S100 | ET | 6095 | 373 | 86 | 223 | 222 |
| Tg resin | °C. | 49 | 44 | 43 | 41 | 37 | 36 | 34 |
| Aromatic H-NMR | % | 6.3 | 4.2 | 13.5 | 11.8 | 9.6 | 11.3 | 4 |
| Aromatic | % | 19 | 13 | 40 | 36 | 28 | 32 | 12 |
| R & B soft. Point | °C. | 94 | 94 | 98 | 89 | 86 | 88 | 85 |
| RBT at +23° C. | cm | 17 | 16 | 17 | 10 | 3.9 | 8.3 | 14 |
| RBT at +15° C. | cm | >30 | >30 | >30 | >30 | 3.8 | 16 | >30 |
| RBT at +10° C. | cm |  |  |  |  | 7 | >30 |  |
| RBT at +5° C. | cm |  |  |  |  | >30 |  |  |

EXAMPLE 5

Table 8 shows the influence of the butadiene-isoprene weight % ratio on the RBT values at different temperatures. The formulations tested were polymer/WINGTACK 86/oil/antioxidant in a ratio 100/110/15/3 based on parts per hundred of rubber. Polymer D is similar to polymer C described in Table 3 but has a butadiene-isoprene weight % ratio of 70-30. Polymer E is similar to polymer C but with a butadiene-isoprene weight % ratio of 30-70. Results indicate the improvement in tack as the butadiene content increases.

TABLE 8

| Formulation | Ingredients | I/B % wt ratio | RBT at 23° C. (cm) | RBT at 15° C. (cm) | RBT at 10° C. (cm) | RBT at 5° C. (cm) |
|---|---|---|---|---|---|---|
| F-20 | Polymer D | 30/70 | 2.1 | 2.6 | 5.9 | 9.4 |
| F-21 | Polymer C | 50/50 | 1.6 | 4 | 3.4 | 23 |
| F-22 | Polymer E | 70/30 | 2.1 | 5.4 | 18 | >>30 |
| F-23 Comp | D-1160 | 100/0 | 12 | >>30 | | |

TECHNICAL FIELD

An adhesive composition comprising
1. one or more styrenic block copolymers,
2. one or more tackifier resins, and
3. one or more plasticizers.

What is claimed is:

1. An adhesive composition for tapes, labels and bandages to be used at temperatures of +5° C. and lower, said adhesive composition comprising
   (a) at least one block copolymer, comprising at least two terminal blocks of poly(vinyl aromatic compound) and at least one midblock of a randomly copolymerized mixture of isoprene and butadiene, wherein the weight ratio between isoprene and butadiene is in the range of from 70:30 to 30:70, optionally mixed with a diblock copolymer comprising one poly(vinyl aromatic compound) block and one randomly copolymerized mixture of isoprene and butadiene, and optionally mixed with a block copolymer, comprising at least one block of poly(vinyl aromatic compound) and at least one block of poly(butadiene) or poly(isoprene),
   (b) at least one mixed aliphatic/aromatic tackifying resin or a blend of aliphatic and aromatic tackifying resins, having an aromatic H-NMR content between 6 and 22%, wherein the tackifying resin has a glass transition temperature Tg between 30° C. and 40° C., and a Ring and Ball softening point between 80° C. and 90° C., and
   (c) a plasticizer in an amount of at most 25 wt %, relative to the weight of the adhesive composition.

2. The adhesive composition of claim 1, wherein said component (a) mainly consists of a S-(I/B)-S or [S-(I/B)]$_n$X block copolymer, optionally mixed with a diblock copolymer S(I/B), and optionally mixed with minor amounts of one or more block copolymers, selected from the group of S-B, S-B-S, S-I and S-I-S, wherein S represents a poly(vinyl aromatic compound) block, (I/B) represents a block of a randomly polymerized mixture of isoprene and butadiene, wherein the weight ratio between isoprene and butadiene is in the range of from 70:30 to 30:70, and wherein B represents a poly(butadiene) block, wherein I represents an poly(isoprene) block.

3. The adhesive composition of claim 2 wherein the contents of S-B, S-I, S-B-S and/or S-I-S block copolymers is in the range of from 0 to 50 wt %, relative to the weight of the component (a).

4. The adhesive composition of claim 1 wherein component (b) has an aromatic H-NMR content between 9 and 22%.

5. The adhesive composition of claim 4 wherein component (b) has an aromatic H-NMR content between 9 and 18%.

6. The adhesive composition of claim 1 wherein component (b) occurs in a proportion of from 35 to 55 wt %, relative to the weight of the composition.

7. The adhesive composition of claim 5 wherein component (b) occurs in a proportion of from 35 to 55 wt %, relative to the weight of the composition.

8. The adhesive composition of claim 1 wherein the S blocks in the block copolymers of component (a) are poly (styrene) blocks and wherein the proportion of bound styrene in the main S-(I/B)-S or [S-(I/B)]$_n$ X block copolymers is in the range of from 10 to 40 wt %.

9. The adhesive composition of claim 7 wherein the S blocks in the block copolymers of component (a) are poly (styrene) blocks and wherein the proportion of bound styrene in the main S-(I/B)-S or [S-(I/B)]$_n$ X block copolymers is in the range of from 10 to 40 wt %.

10. Tape, labels and bandages, comprising a substrate layer and an adhesive composition applied thereon, said adhesive composition comprising
    (a) at least one block copolymer, comprising at least two terminal blocks of poly(vinyl aromatic compound) and at least one midblock of a randomly copolymerized mixture of isoprene and butadiene, wherein the weight ratio between isoprene and butadiene is in the range of from 70:30 to 30:70, optionally mixed with a diblock copolymer comprising one poly(vinyl aromatic compound) block and one randomly copolymerized mixture of isoprene and butadiene, and optionally mixed with a block copolymer, comprising at least one block of poly(vinyl aromatic compound) and at least one block of poly(butadiene) or poly(isoprene),
    (b) at least one mixed aliphatic/aromatic tackifying resin or a blend of aliphatic and aromatic tackifying resins, having an aromatic H-NMR content between 6 and 22%, wherein the tackifying resin has a glass transition temperature Tg between 30° C. and 40° C., and a Ring and Ball softening point between 80° C. and 90° C., and
    (c) a plasticizer in an amount of at most 25 wt %, relative to the weight of the adhesive composition.

11. Tapes, labels and bandages comprising a substrate layer and an adhesive composition applied thereon, wherein said tapes labels and bandages are used at temperatures of +5° C. or lower and said adhesive composition comprises:
    (a) at least one block copolymer, comprising at least two terminal blocks of poly(vinyl aromatic compound) and at least one midblock of a randomly copolymerized mixture of isoprene and butadiene, wherein the weight ratio between isoprene and butadiene is in the range of from 70:30 to 30:70, optionally mixed with a diblock copolymer comprising one poly(vinyl aromatic compound) block and one randomly copolymerized mixture of isoprene and butadiene, and optionally mixed with a block copolymer, comprising at least one block of poly(vinyl aromatic compound) and at least one block of poly(butadiene) or poly(isoprene),
    (b) at least one mixed aliphatic/aromatic tackifying resin or a blend of aliphatic and aromatic tackifying resins, having an aromatic H-NMR content between 6 and 22%, wherein the tackifying resin has a glass transition temperature Tg between 30° C. and 40° C., and a Ring and Ball softening point between 80° C. and 90° C., and
    (c) a plasticizer in an amount of at most 25 wt %, relative to the weight of the adhesive composition.

* * * * *